US009216421B2

(12) United States Patent  (10) Patent No.: US 9,216,421 B2
Gordon  (45) Date of Patent: Dec. 22, 2015

(54) INTEGRATED SYSTEM FOR SAMPLING AND ANALYSIS

(75) Inventor: Julian Gordon, Lake Bluff, IL (US)

(73) Assignee: Inspirotec LLC, Glenview, IL (US)

( * ) Notice: Subject to any disclaimer, the term of this patent is extended or adjusted under 35 U.S.C. 154(b) by 580 days.

(21) Appl. No.: 13/559,911

(22) Filed: Jul. 27, 2012

(65) Prior Publication Data

US 2013/0029408 A1  Jan. 31, 2013

Related U.S. Application Data

(60) Provisional application No. 61/512,740, filed on Jul. 28, 2011.

(51) Int. Cl.

| | |
|---|---|
| *G01N 27/327* | (2006.01) |
| *B03C 3/36* | (2006.01) |
| *G01N 1/40* | (2006.01) |
| *B03C 3/12* | (2006.01) |
| *B03C 3/41* | (2006.01) |
| *B03C 3/47* | (2006.01) |
| *G01N 1/22* | (2006.01) |
| *G01N 33/497* | (2006.01) |

(52) U.S. Cl.
CPC . *B03C 3/366* (2013.01); *B03C 3/12* (2013.01); *B03C 3/41* (2013.01); *B03C 3/47* (2013.01); *G01N 1/2273* (2013.01); *G01N 1/40* (2013.01); *B03C 2201/26* (2013.01); *G01N 33/497* (2013.01); *G01N 2001/2285* (2013.01)

(58) Field of Classification Search
CPC ............ G01N 2001/2285; G01N 1/2273; G01N 2001/2244; G01N 1/2247; G01N 1/2214; G01N 2001/2223; G01N 33/497; G01N 33/4972; G01N 2033/497; G01N 2033/4977; A61B 5/08; A61B 5/082
See application file for complete search history.

(56) References Cited

U.S. PATENT DOCUMENTS

| | | | | |
|---|---|---|---|---|
| 5,309,085 | A  * | 5/1994 | Sohn | 257/253 |
| 6,951,715 | B2 * | 10/2005 | Cunningham et al. | 435/4 |
| 7,217,574 | B2 * | 5/2007 | Pien et al. | 436/164 |
| 8,038,944 | B1 * | 10/2011 | Gordon et al. | 422/82.01 |
| 2003/0027214 | A1 * | 2/2003 | Kamb | 435/7.1 |
| 2004/0083790 | A1 * | 5/2004 | Carlson et al. | 73/28.02 |
| 2004/0181344 | A1 * | 9/2004 | Stephanopoulos et al. | 702/20 |
| 2007/0231926 | A1 * | 10/2007 | Ikeda | 436/526 |
| 2009/0149340 | A1 * | 6/2009 | True | 506/9 |
| 2009/0170072 | A1 * | 7/2009 | Mink et al. | 435/5 |

FOREIGN PATENT DOCUMENTS

EP  1645865 A1 *  4/2006  ............ G01N 21/45

* cited by examiner

*Primary Examiner* — Alexander Noguerola
(74) *Attorney, Agent, or Firm* — Wood, Phillips, Katz, Clark & Mortimer

(57) ABSTRACT

There is disclosed a device for determination of a sample from a dielectric fluid medium for a bio-specific assay device, comprising: a sampling device and a biosensor, wherein the sampling device concentrates a sample from dielectric medium by electrically focusing the sample on to a capture element and wherein said biosensor is fluidically linked to said capture element thus providing sampling and determination in a unitary device.

14 Claims, 6 Drawing Sheets

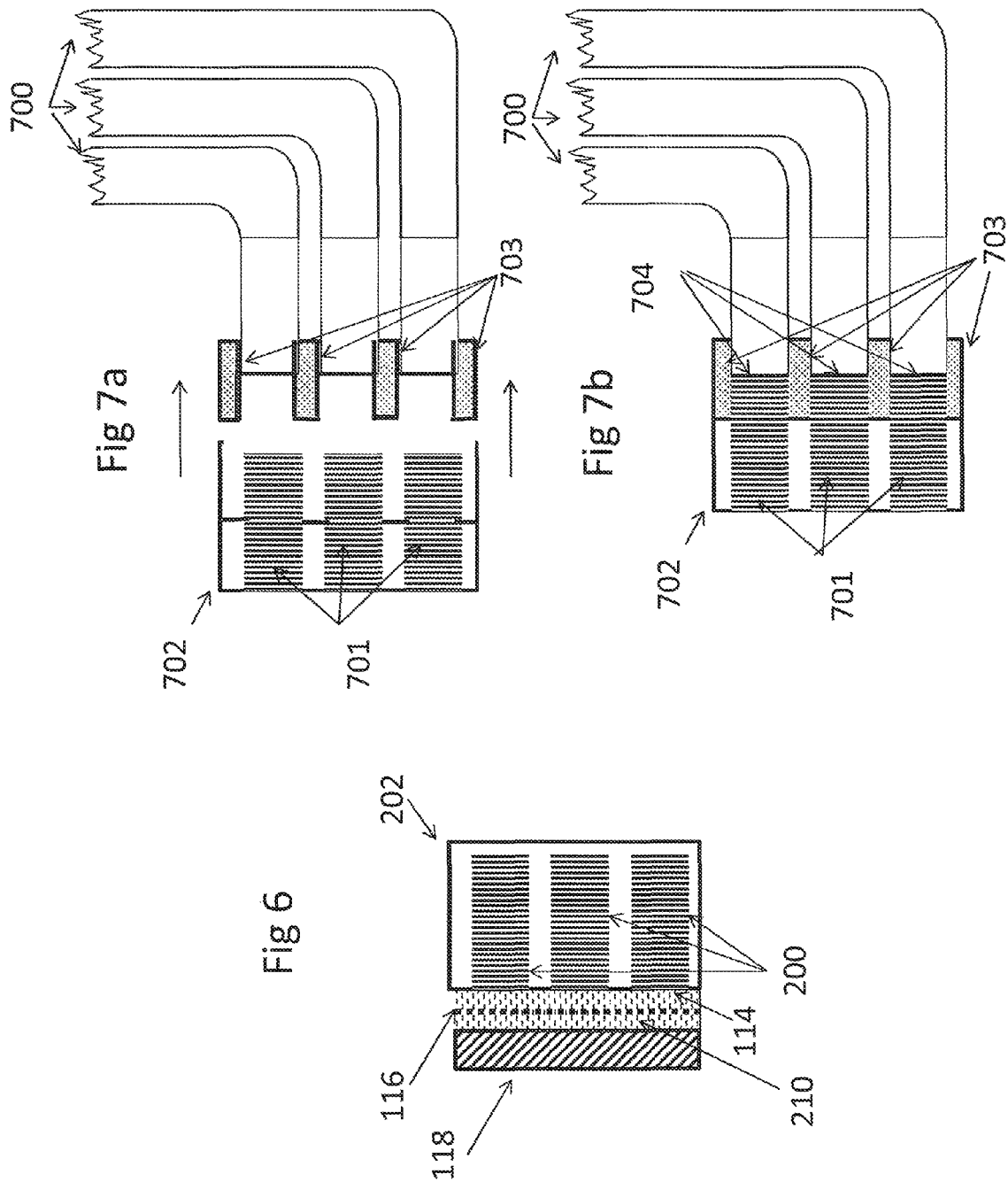

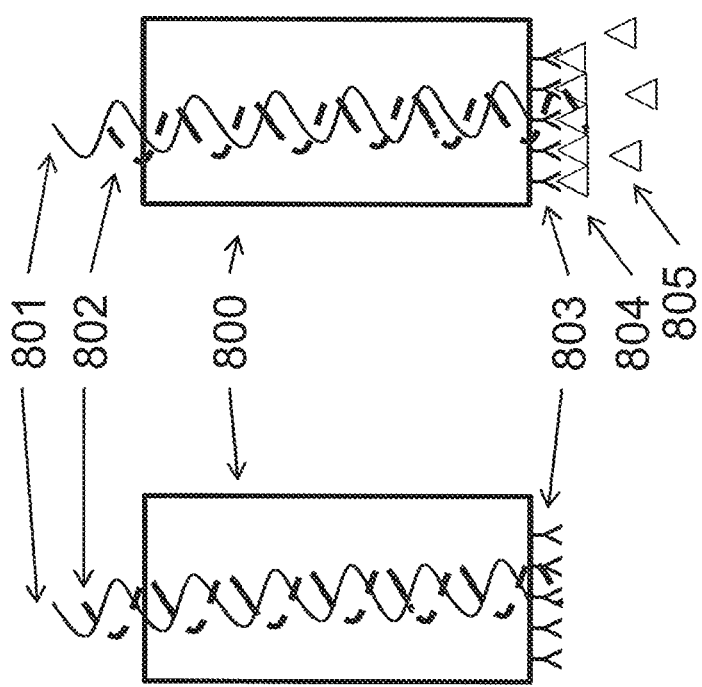

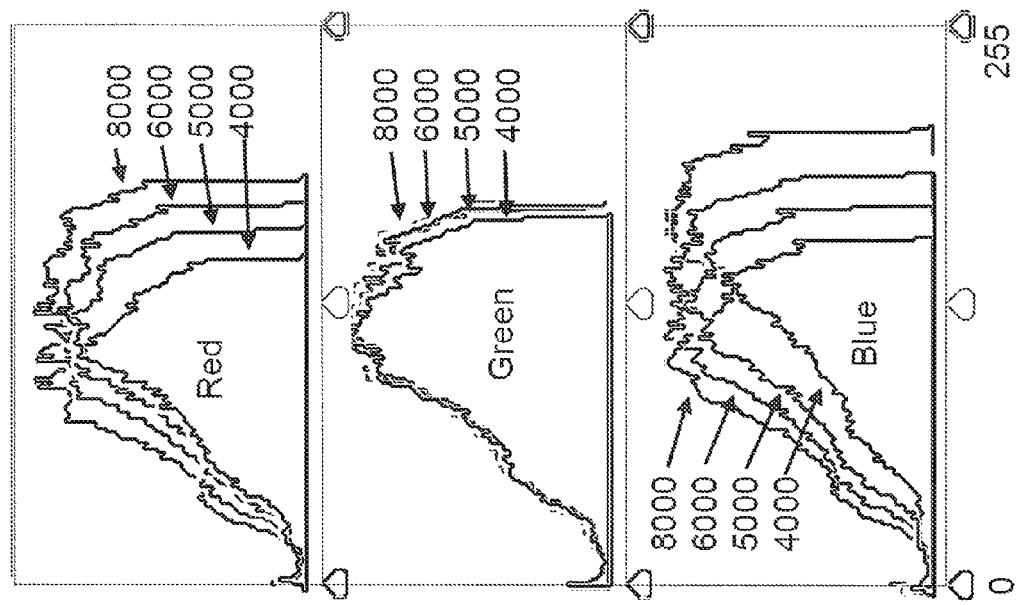

INTEGRATED SYSTEM FOR SAMPLING AND ANALYSIS

CROSS-REFERENCE TO RELATED APPLICATIONS

This application claims priority of provisional application No. 61/512,740 filed Jul. 28, 2011.

FEDERALLY SPONSORED RESEARCH OR DEVELOPMENT

Not Applicable.

MICROFICHE/COPYRIGHT REFERENCE

Not Applicable.

FIELD OF THE INVENTION

The invention relates to the collection of and sampling of assayable agents in a dielectric medium and, more particularly, integrating the collection system with an assay system requiring no mechanical or chemical procedural steps except for the optional addition of a suitable liquid.

BACKGROUND

In the prior art, there exist many examples of collection of agents from the air for bioassay. For example, the following publications describe various methods of allergen, pathogen and toxin collection for assay: Yao et al (2009) in Aerosol Science volume 40, pages 492-502;

Noss et al (2008) in Applied and Environmental Microbiology, volume 74, pages 5621-5627;

King et al (2007) in Journal of Allergy and Clinical Immunology, volume 120, pages 1126-31;

Earle et al (2007) in Journal of Allergy and Clinical Immunology, volume 119, pages 428-433;

Peters et al (2007) in Journal of Urban Health: Bulletin of the New York Academy of Medicine, volume 84, pages 185-197;

Yao and Mainelis (2006) in Journal of Aerosol Science, volume 37, pages 513-527;

Platts-Mills et al (2005) in Journal of Allergy and Clinical Immunology, volume 116, pages 384-389;

Sercombe et al (2004) in Allergy, volume 60, pages 515-520;

Custis et al (2003) in Clinical and Experimental Allergy, volume 33, pages 986-991;

Polzius et al (2002) in Allergy, volume 57, pages 143-145;

Tsay et al (2002) in Clinical and Experimental Allergy, volume 32, pages 1596-1601;

Parvaneh et al (2000) in Allergy, volume 55, pages 1148-1154; and

McNerney et al (2010) in BMC Infectious Diseases, volume 10, pages 161-166 and device in U.S. Pat. No. 7,384,793.

Other known methods of sample collection include trapping of volatile organic compounds (VOC) on activated carbon, de-sorption and analysis by mass spectrometry. See Phillips at al (2010) in Tuberculosis, volume 90, pages 145-151 and references therein. VOC's are not considered encompassed by the present invention since the assays are strictly chemical in nature, and are not bio-specific as defined here. By bio-specific assays is meant assays wherein the result is determined by a biological specificity such as nucleic acid specificity, antibody specificity, receptor-ligand specificity and the like. While diagnostic specificity may be achieved by VOC analysis, this is inferred by presence and amount of groups of defined organic compounds.

The foregoing prior art publications describe "dry" methods using pumping and filtration, wiping, passive deposition, electrokinetic transport etc; usually followed by an extraction step and application of the extract to an assay.

Methods for collection in a liquid stream have been described in the patent literature including Yuan and Lin in US Patent Application 2008/0047429A1, and Bashi at al. in U.S. Pat. No. 6,484,594. While efficiently collecting agents from the air, such liquid streaming systems inevitably result in high dilution of the sample. There is a consequent trade-off in sensitivity unless the agents are re-concentrated.

Northrup et al. in U.S. Pat. Nos. 7,705,739 and 7,633,606 describe an autonomously running system for air sampling and determination of airborne substances therein. They do not specify the exact method of air sampling, nor detail how it is transferred to an assay system.

There exist numerous commercially available systems for air purification based on filtration or electrostatic precipitation. For a general description see the Environmental Protection Agency article "Guide to Air Cleaners in the Home", U.S. EPA/OAR/ORIA/Indoor Environments Division (MC-6609J) EPA 402-F-08-004, May 2008. Numerous commercial examples of systems exist using either High Efficiency Particulate Air (HEPA) filters or electrostatic precipitation filters. Such systems are widely used for removal of particulate matter or allergens from air, including as part of domestic heating, ventilation and air conditioning (HVAC) systems. HEPA filters have the advantage of removal of particles down to the micron size range, whereas electrostatic precipitation methods have the advantage of entailing high volume flow with little or no pressure differential. See US patent by Bourgeois, U.S. Pat. No. 3,191,362 as a detailed example for the technical specification of an electrostatic precipitation system. While efficiently removing agents from the air, such air purification systems do not lend themselves to collection of samples for analysis.

Electrokinetic-based air cleaning systems have been developed and formerly commercialized by the company Sharper image under the trade name Ionic Breeze. The original electrokinetic principle was enunciated by Brown in U.S. Pat. No. 2,949,550. This was further improved by Lee in U.S. Pat. No. 4,789,801 for improving airflow and minimizing ozone generation. Further improvements for the commercially available system are described in US patents by Taylor and Lee, U.S. Pat. No. 6,958,134; Reeves et al, U.S. Pat. No. 7,056,370; Botvinnik, U.S. Pat. No. 7,077,890; Lau et al, U.S. Pat. No. 7,097,695; Taylor et al, U.S. Pat. No. 7,311,762. In the foregoing descriptions of devices using electrokinetic propulsion, a common element is a high voltage electrode consisting of a wire. A very steep voltage gradient is generated orthogonally to the wire because of the very small cross-sectional area of the wire. The high voltage gradient causes the creation of a plasma consisting of charged particles, and kinetic energy is imparted to the charged particles by the high voltage gradient. The resulting net air flow is created by exchange of kinetic energy between charged and uncharged particles, and the net air flow is directed by the juxtaposition of planar electrodes which are at zero or opposite sign voltage to that of the wire electrode. Charged particles are electrostatically precipitated on to the planar electrodes which may periodically be removed for cleaning. This body of work is directed toward air purification not sample collection. However, as first described by Custis et al. (2003), the Ionic Breeze device has been adapted for sample collection for allergen analysis by wiping down the electrodes with a paper tissue. The allergens were extracted from the tissue and subject to an immunoassay. The Ionic Breeze was also used in the works of Peters et al. (2007) and Platts-Mills et al. (2005) for allergen collection for immunoassay analysis. Earlier, Parvaneh et al. (2000) described an ionizer device with a "metal cup having a conductive surface as a collector plate", from which allergens are extracted for assay. It is not evident how the sample is collected on the inside of a metal cup and does not adhere to the entire surface. The device was made by Airpoint AB, Stockholm, Sweden. However, there is no public information concerning the manufacture or sale of such a product by Airpoint AB, there is insufficient information for one skilled in the art to be able to understand the details of the device, and no similar device was used by the same authors in subsequent publications on environmental allergen detection. There is no mention of focusing of the sample into a potential well created by a voltage gradient.

Yao et al (2009) and Yao and Mainelis (2006) have described methods for collection of bio-assayable agents on to an assay means or device. Yao and Manielis (2006) describe blocks of agar gel in electrical contact with planar electrodes, and Yao et al (2009) describe a microtiter plate interposed between planar electrodes. Both of these works describe a flow of air driven by a pump, and electrostatically precipitating the agents to be analyzed on to the assay means. The electrodes and the agar blocks have substantially the same area in these works.

McNerney et al (2010) describe a breathalyzer device, where the individual breathes or coughs into a breathing tube, the sample collects on the internal surface of a tube, is scraped with a plunger on to an optical biosensor, an immunological binding reaction is performed and the biosensor utilizes an evanescent wave illumination system to determine the presence or absence of *M. tuberculosis* by scattered light.

None of the above methods consider the use of an electric field gradient forming a potential well to focus the agents on to a collection means for an assay device.

A vast number of assay methods for immunoassays and nucleic acid hybridization assays are well-known in the art, of varying complexity, of which there are too many to review here. The large majority require some label to achieve a detectable signal. The label may be radioactive, fluorescent, enzyme with chromogenic substrate, enzyme with electroactive product to produce an electrical signal. Such methods have revolutionized assay procedures, but require inconvenient interception with protocol steps for washing and removing unbound agents and unbound label. More appropriate are self-performing or dip-stick assays. Lateral flow self-performing assays still require a label, usually dried within the device, which then reveals a positive result when the label is bound at a specific site on the lateral flow strip, and appears as the localized concentration exceeds the concentration of the flowing unbound label Lateral flow assays are reviewed comprehensively by Gordon and Michel, see 1, below. Further assays are known which require no label and use the modification of the optical properties of a binding surface, see refs 2-10 below.

1. Gordon J, Michel Analytical sensitivity limits for lateral flow immunoassays. Clinical Chemistry. 2008; 54(7):1250-1.
2. Brecht A, Ingenhoff J, Gauglitz G. DIRECT MONITORING OF ANTIGEN-ANTIBODY INTERACTIONS BY SPECTRAL INTERFEROMETRY. Sensors and Actuators B-Chemical. 1992; 6(1-3):96-100.
3. Gauglitz G, Brecht A, Kraus G, Nahm W. Chemical and Biochemical Sensors Based on Interferometry at Thin (Multi-)Layers. Sensors and Actuators B-Chemical, 1993; 11(1-3):21-7.
4. Cunningham B, Li P, Lin B, Pepper J. Colorimetric resonant reflection as a direct biochemical assay technique. Sensors and Actuators B-Chemical. 2002; 81(2-3):316-28.
5. Petrou P S, Ricklin D, Zavali M, Raptis I, Kakabakos S E, Misiakos K, et al. Real-time label-free detection of complement activation products in human serum by white light reflectance spectroscopy. Biosensors and Bioelectronics. 2009; 24(11):3359-64.
6. Concepcion J, Witte K, Wartchow C, Choo S, Yao D F, Persson H, et al. Label-Free Detection of Biomolecular Interactions Using BioLayer Interferometry for Kinetic Characterization. Combinatorial Chemistry & High Throughput Screening 2009; 12(8):791-800.
7. Zavali M, Petrou P S, Goustouridis D, Raptis I, Misiakos K, Kakabakos S E. A regenerable flow-through affinity sensor for label-free detection of proteins and DNA ☆. Journal of Chromatography B. 2010; 878(2):237-42.
8. Zavali M, Petrou P S, Kakabakos S E, Kitsara M, Raptis I, Beltsios K, et al. Label-free kinetic study of biomolecular interactions by white light reflectance spectroscopy. Micro & Nano Letters. 2006; 1(2):94.
9. Abdiche Y, Malashock D, Pinkerton A, Pons J. Determining kinetics and affinities of protein interactions using a parallel real-time label-free biosensor, the Octet. Analytical Biochemistry. 2008; 377(2):209-17.
10. Abdiche Y N, Malashock D S, Pinkerton A, Pons J. Exploring blocking assays using Octet, ProteOn, and Biacore biosensors. Analytical Biochemistry. 2009; 386(2):172-80.

Further US patents by Chen (U.S. Pat. No. 5,804,453) and Tan at al. (U.S. Pat. No. 7,656,536) describe label free methods utilizing fiber optics. A recent application of label-free direct binding technology is the Octet system of Fortebio (Pall ForteBio Corp, Menlo Park, Calif.). The Octet system is designed for immersing eight analyte-specific biosensor probes based on fiber optics into separate wells of a microwell plate and directly observing binding of the analyte molecules from the wavelength shift produced by interference between incoming and reflected light, by means of a spectrophotometer. This is thus a true dipstick assay method.

Thus, while many of the above elements are known or commercially available, there is a need for a simple portable integrated system. Such a system could be used by consumers or public health practitioners for determining the presence of allergens or pathogens in buildings. Such a system could easily be deployed in public environments for the monitoring and early recognition of pandemics, such as influenza pandemics. Such a system could be deployed at international transit points and points of entry for early recognition of bioterrorism agents. Such a system could be used by military personnel in the field for early detection of biowarfare agents.

The present invention is directed to improvements over the systems and methods noted above.

SUMMARY

Thus, there is disclosed herein a device for determination of a sample from a dielectric fluid medium for a bio-specific assay device, comprising: a sampling device and a biosensor, wherein the sampling device concentrates a sample from dielectric medium by electrically focusing the sample on to a capture element and wherein said biosensor is fluidically linked to said capture element thus providing sampling and determination in a unitary device.

The sampling device may comprise an ionic propulsion device and focuses the sample on to a delimited area. The delimited area results in sample concentration and interrogation of a small volume thus resulting in improved sensitivity.

The biosensor may comprise an optical sensor device. The optical sensor device may be a white light interference spectroscopy device. The optical sensor device may be a fluorescent microparticle-based sensing system.

The biosensor may comprises an electrical sensing device, such as a field-effect transformer device or a magneto-resistive device.

The optical sensor device may measures shifts in wavelength light, optical interference, or color of fluorescent microparticles. The wavelength shift may be determined by means of a spectrophotometer, by a digital imaging device, or from color values of pixels.

There is also disclosed an optical biosensor device wherein molecular binding reactions are determined by analysis of spectral changes in digital images. The spectral changes may result from optical interference effects or from fluorescent microparticle binding reactions. The spectral changes may be determined from analysis of color value distributions of pixels.

The present invention relates generally to (1) the use of electrokinetic means of concentrating a sample from a fluid stream on to a capture material, (2) self-performing bio-specific assay of sample on capture material and (3) determination of a result by camera imaging and image analysis software. The invention also encompasses methodology for combining these three elements into a unitary device. Co-owned U.S. Pat. No. 8,038,944, describes the elements of an electrokinetic means of concentrating a sample to be analyzed on to a capture material. This patent also discusses the combination of the capture material with a variety of bio-specific assays. The present invention focuses on assay means that run autonomously with few or no steps in the assay procedure, either automated or manual, and minimal number or no reagent addition steps. Especially preferred are methods where no label is required, but molecular interactions are determined directly and transduced into signals that can be captured by a camera or camera-like device, and computation of a result via imaging and image processing software.

Suitable assays include lateral flow immunochromatography assays where labeled antibody is deposited in a dry state and the signal is generated as color at a defined analyte-detection site on the strip. The color signal is then focused on to the image plane of a camera lens and the presence, amount or absence of color determined by image analysis software. Further suitable assays are those involving reflectance-interference analyses, where there is interference between incoming light and light reflected from an optical interface. In that case, white light is subject to a wavelength shift which is captured by the image plane of a camera lens and the shift in color analyzed by on-board image analysis software, and the presence, amount or absence of analyte determined by the image analysis. Multiplex capabilities are also incorporated in the invention. In the two proposed approaches, this can be achieved by multiple parallel lateral flow immunoassays or multiple optically active surfaces interrogated by reflectance-interference analysis. Especially useful is the use of fiber optics, because of their flexibility and ease of multiplexing. They may be created in the form of bundles with each member of the bundle having a different binding-specific agent deposited on an optically active tip.

Other features and advantages will be apparent from a review of the entire specification, including the appended claims and drawings.

BRIEF DESCRIPTION OF THE DRAWINGS

FIG. 6. illustrates an alternate geometry for introduction of liquid to effect solution of captured material and binding reaction to optical interface;

FIG. 7. illustrates interfacing of a removable tip with bio-specific optical interfaces and cladded ends of fiber optics;

FIG. 8 illustrates the principle of white light interference spectroscopy;

FIG. 10. illustrates spectral shifts from intensity distribution of pixels.

DETAILED DESCRIPTION

Figure 1:
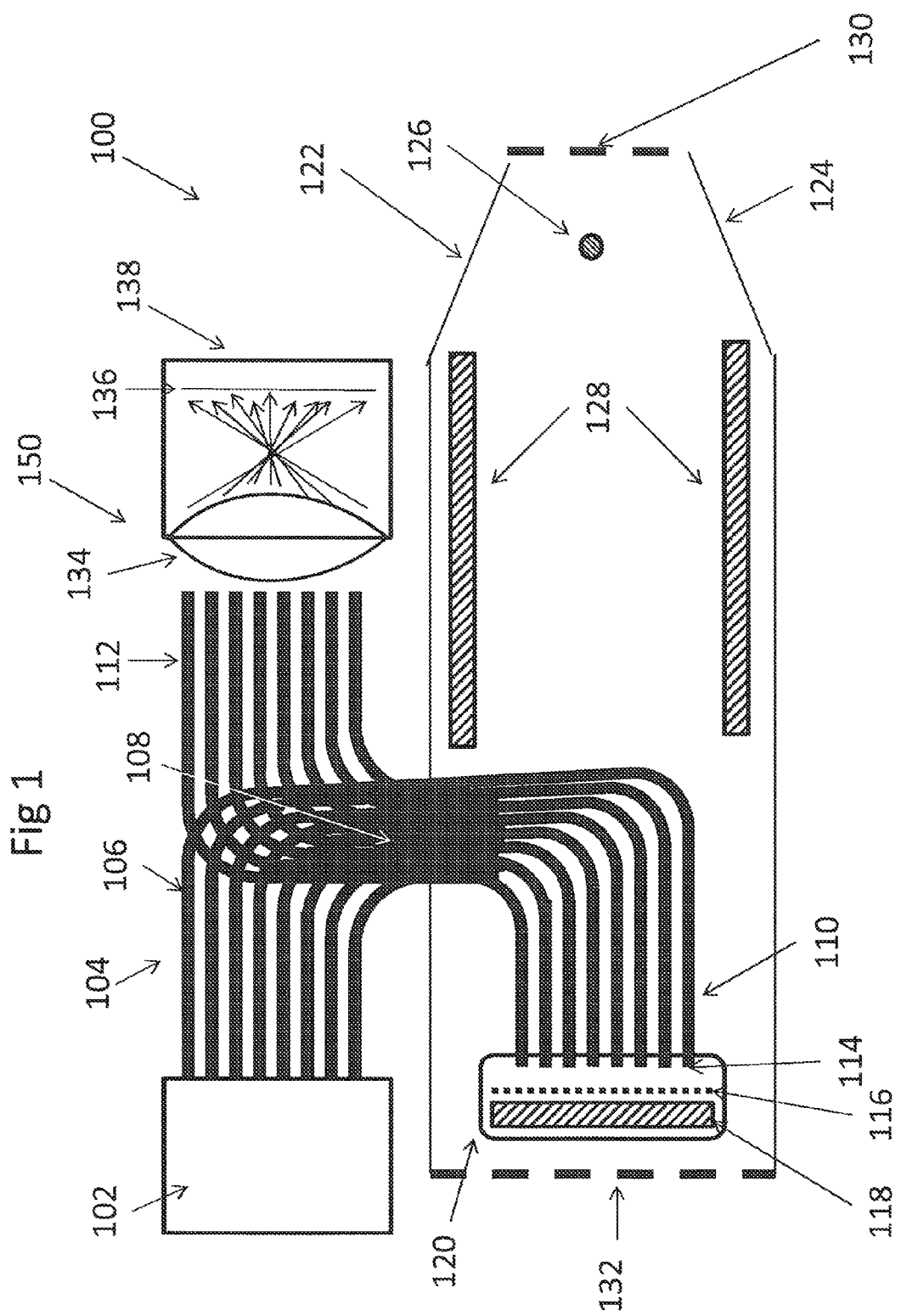
FIG. 1. illustrates an overview of an integrated system combining air sampling, sample capture and detection technology.

The present invention relates to the collection of and sampling of assayable agents in a dielectric medium, usually air and, more particularly, integrating the collection system with an assay system requiring no mechanical or chemical procedural steps except for the optional addition of a suitable liquid. This includes, but is not limited to, sampling air for agents whose presence, absence or amount is determined by bio-specific assays. The field includes sampling of air for biological agents, direction to, and deposition on, a collection means for an assay device integrated with a detection device. The bio-specific assays may include immunoassays, nucleic acid hybridization assays, or any other assays entailing ligand-antiligand interactions. Assays are of the true dipstick type, or may be of the self-performing lateral flow type, resulting in the direct transduction of a binding event signal to an assay result. Agents assayed include, but are not limited to bio-warfare agents, pathogens, allergens or pollutants. Pathogens include screening for infectious airborne agents such as anthrax or tuberculosis organisms. Further dielectric media may include sampling of dielectric fluid medium such as oil for the food industry, or petrochemical and industrial oil.

Devices and methods are described with the purpose of integrating the processes of sample collection and analyte detection for bio-specific assays. Electrokinetic flow may be induced by the use of plasma generation at high voltage electrodes and consequent transport of charged particles in an electric voltage gradient. Agents are directed electrokinetically on to a sample collection material at the sample collection zone with no intermediate transfer steps. The agents are directed by creation of an electrokinetic potential well or wells, which will effect their capture on to an assay device. Agents are then directed seamlessly from collection zone to an assay zone, where dipstick or other simple technology is used to transduce a binding reaction into a detectable signal. Environmental agents such as biowarfare agents, pathogens, allergens or pollutants are collected autonomously on to the assay device, where bio-specific elements bind the agent to be detected and thus effect a detectable signal. The only external intervention is, following the sample collection phase, the initiation of the transfer and binding reaction steps, by introduction of a suitable assay liquid with no other mechanical or protocol steps. The sample collection phase may be terminated and assay phase initiated either manually or automatically. The assay phase is initiated by introduction of a suitable assay liquid, which may be stored on-board in the device and transported into the assay zone as needed.

In one embodiment, the detection step is carried out by an interference-reflectance device utilizing the binding at planar interface to a fiber-optic element. The light source may be a white light source and can comprise a flash discharge device and wavelength shifts determined spectrophotometrically. Images may be captured by CCD or CMOS camera devices and wavelength shifts determined by image analysis procedures. Devices may be multiplexed indefinitely by the use of multiple optical fibers, and analysis of the multiple fiber outputs performed by image analysis software.

FIG. 1 illustrates a device 100 in accordance with the invention for determination of a sample form a dielectric fluid medium for a bio-specific assay device. The device 100 comprises a light source 102 operatively associated with a fiber optic system 104 here shown for an octoplex detection system. The fiber optic system 104 includes a first set 106 of optical fibers connected via a bifurcation device 108 to a second set 110 and a third set 112 of optical fibers. The second set 110 of optical fibers terminate at an interface 114. As configured, light from the light source 102 travels via the first set 104 of optical fibers through the bifurcation device 108 to the second set 110 of optical fibers to the interface 114. Reflected light at the interface 114 travels via the second set 110 of optical fibers through the bifurcation device 108 to the third set 112 of optical fibers. Such structure is well known in the art.

The second set 110 of optical fibers terminate at the Interface 114 in proximity to a non-conducting capture element or material 116 which overlays a capture electrode 118. Ends of the optical fibers of the second set 110 may be coated with an optical layer and binding agent to define the interface 114, as is known. The capture material 116 and optical fiber interface 114 are in a non-conducting vessel 120 which selectively enables liquid contact between the interface 114 and the capture material 116.

An ionic collection device 122 includes a housing 124 enclosing the vessel 120 and related elements, discussed above. Also included in the housing 124 are a wire electrode 126, guiding electrodes 128 and the capture electrode 118. The housing 124 includes an entrance grille 130 and an exit grille 132. The ionic collection device 122 may be in accordance with the various teachings of U.S. Pat. No. 8,038,944, owned by the assignee of the present application, and the specification of which is incorporated by reference herein.

As described herein, such a collection device is adapted to include detection apparatus in the form of a biosensor 150. The biosensor 150 includes the light source 102 and the optical fiber system 104. Totally internally reflected light from the optical interface 114 is returned via the bifurcation device 108 and the third set 112 of optical fibers to an objective lens 134 and focused on a focal plane 136 of an optical sensor system 138, such as a CCD or CMOS based camera system. The optical sensor system 138 could take other known forms, as described below.

The Octet system of Fortebio Inc has many features which would be useful here, including a fiber optic system similar to that shown herein, although the manufacturers only commercialize it for use on microplates. The use of a camera system 138 including image analysis obviates the use of the bulky spectrophotometer used with the Octet system. Further, the Octet has eight analyte specific separate probes. Here, the probes could be integrated into a unitary replaceable device which interfaces with the capture material 116.

The optical fiber system 104 and vessel 120 may appear to obstruct the flow of air through the housing 124, but this is partly due to the requirement for simplicity and intelligibility of the drawing. In practice, they could be deployed to one side in third dimension, out of the way of the main stream. Or they may be moveably deployed outside of the main stream, and only rotated or otherwise deployed into place after collection of the sample on to the capture material 116. The act of deployment could further be used as a simple way of initiating the flow of assay liquid into vessel 120 to initiate the release of the captured sample into solution and the initiation of a binding reaction at the interfaces 114. This deployment could be effected manually or automatically.

The light source 100 may be any white light, source, such as incandescent or fluorescent lamp. Laser or LED sources may also be used. It can advantageously be a camera flash or strobe device. In that case, multiple flashes are used to obtain multiple time points during the course of the binding reaction. Measurement of binding rates has many well-known advantages over measurement of end points, such as elimination of background and baseline corrections, and improved signal-to-noise. Similar considerations apply to any self-performing assay format used in the current invention, including the time course of appearance of signal in the analyte capture position of a lateral flow immunoassay.

The objective lens 134 may be replaced by a complex lens system, such as a macro lens, so as to provide enlarged images of the light emerging from the termini of the fibers.

Figure 2:
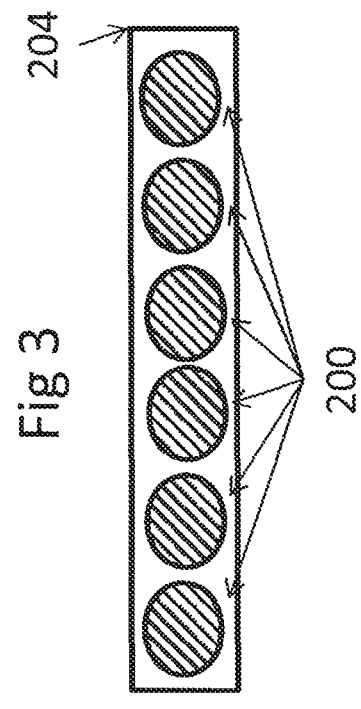
FIG. 2. illustrates an arrangement of optical fibers for hexaplex detection.
Figure 3:
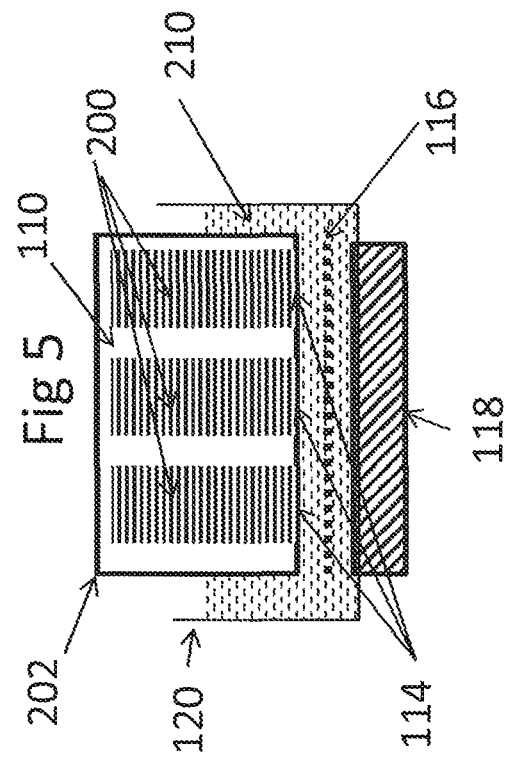
FIG. 3. illustrates an alternative arrangement of optical fibers for hexaplex detection.

FIG. 2 shows how individual optical fibers 200 of the optical fiber system 104 of FIG. 1 may be arranged within a cladding 202 for a hexaplex system. Similarly, FIG. 3 shows an alternative arrangement of the fibers 200 within the alternative cladding 204 also for a hexaplex system.

Figure 4:
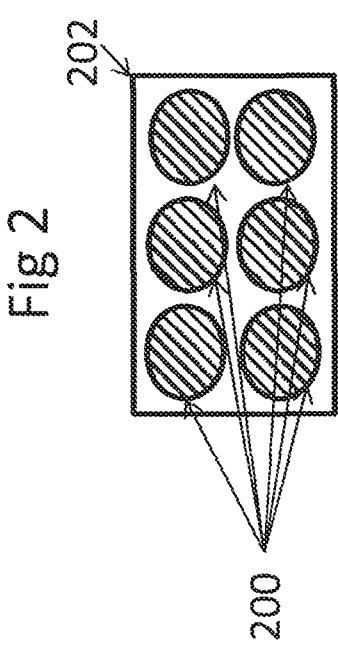
FIG. 4. illustrates a surrounding non-conducting vessel to effect a liquid contact between capture material and optical interface of optical fibers.
Figure 5:
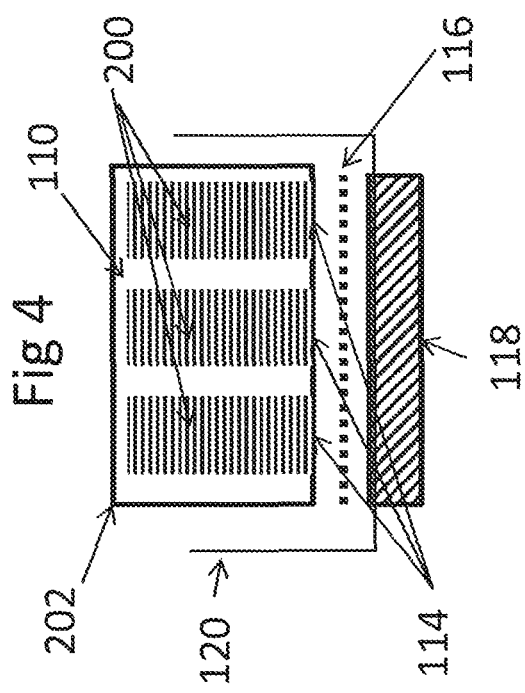
FIG. 5. illustrates introduction of liquid to effect solution of captured material and binding reaction to optical interface.

FIG. 4 shows in more detail the juxtaposition of the interface or termini 114 of the optical fibers 200, of the second set 110, with respect to the capture material 116 and capture electrode 118 in the non-conducting containment vessel 120. This structure permits fluid contact with the capture material 116 and optical fiber termini 114. FIG. 5 is essentially similar to FIG. 4 except with the addition of assay fluid 210 to the containment vessel 120.

FIG. 6 illustrates an alternative orientation of the geometry of the device relative to that in FIG. 5 for providing the liquid contact between the capture material 116 and the optical fiber termini 114.

FIGS. 7a and 7b show how termini with different biospecific labels can be removably attached to the body of optical fibers 700 to be replaced for successive tests. Removable fiber extensions 701, with individually coated interfaces with binding agents in a housing 702, engages with cladding extensions 703, which engage with slots in removable part, such that when the parts are combined, see FIG. 7b, there is an optical connection between the removable part and the fixed part, 704. A collection of removable tips may be mounted in a standardized plastic holder and be a disposable or re-useable element. Conditions for re-use are described in ref 7 above.

FIG. 8 illustrates the principle of white light interference spectroscopy with a fiber optic element 800 with an incident light wave 801 and a reflected light wave 802. Specific antibodies 803 are coated on an active tip surface of fiber optic element. Antigens 804, when present, will bind to specific antibodies 803, and some fraction, 805, may remain unbound. The presence of bound antigens 804 increases the effective optical path and hence the phase relationship between the incident and the reflected waves. This results in a shift in the spectrum of the resultant wave detected by a camera or a spectrophotometer. For the purposes of this illustration, only one wavelength is shown. However, when white light is used as the source, the entire spectrum will be shifted according to the optical path presented by the bound antibody or the bound antibody-antigen complex. Note that material that is not bound, 805, does not affect the optical path and therefore no wash steps are required for removal of unbound material. As soon as binding reactions occur, the effective optical path changes and the resultant spectral shift can be determined in real time.

Figure 9:
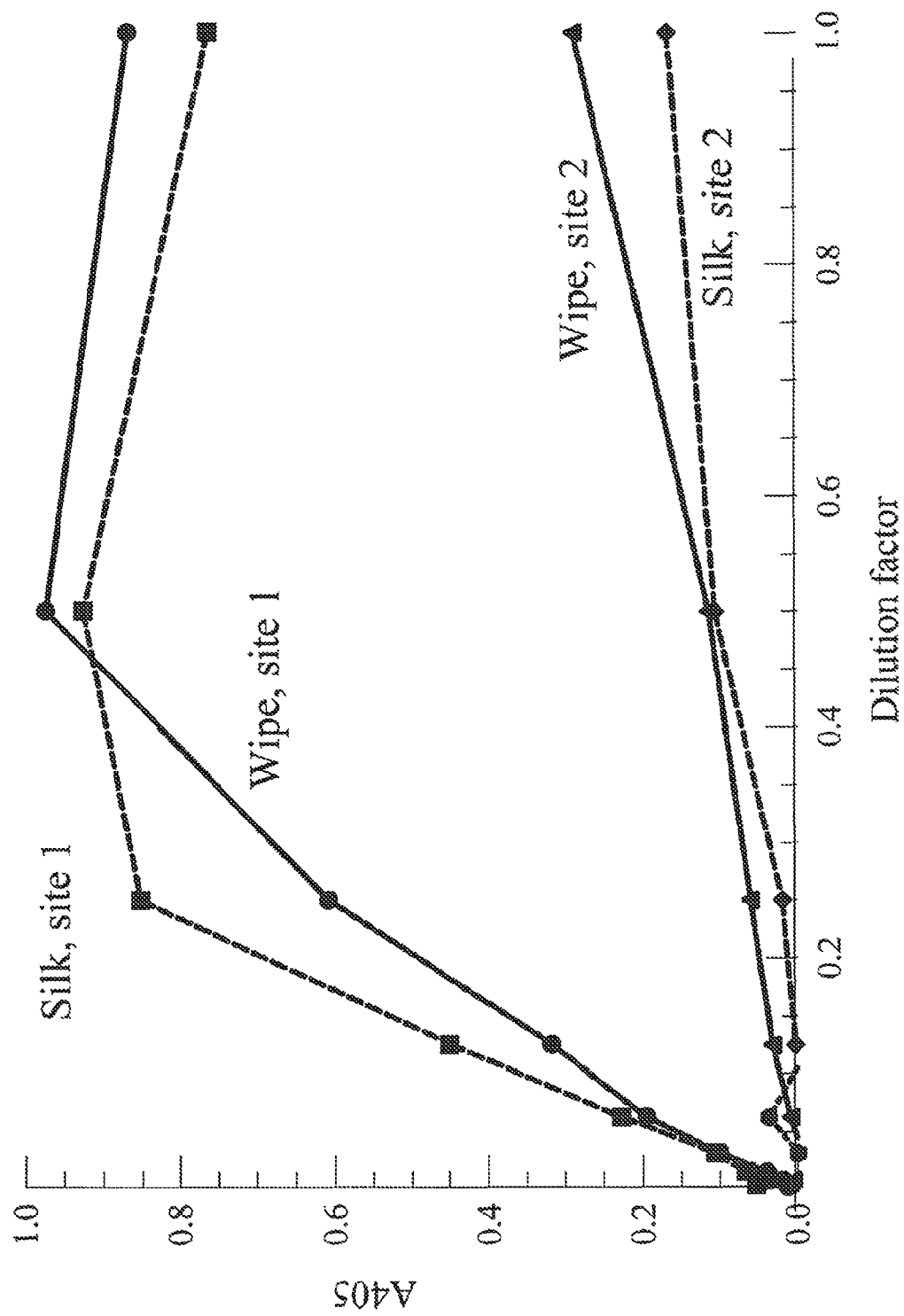
FIG. 9. Illustrates an ELISA test of cat allergen with capture material.

FIG. 9 is a demonstration of the efficacy of a capture material, silk, in conjunction with the electrodes of a commercial Ionic Breeze device. Devices were run in site 1 and site 2, and samples were collected by immersing the silk in a liquid and subjecting the liquid to an ELISA assay for the presence of cat allergens. Control devices were also run and the electrodes wiped down with a moistened tissue. Full experimental details will be provided as Example 1.

FIG. 9 demonstrates the efficacy of a CMOS-sensor based digital camera to quantitate spectral shifts. The program Adobe Bridge was used to simulate illumination of a white material with light sources of color temperatures of 4000, 5000, 6000 and 8000 degrees. Plots show distribution curves from Adobe Photoshop of pixel intensities in red, green and blue channels in a scale of 1 to 255 for the different simulated color temperatures. Full experimental details will be provided as example 2.

Example 1 comprises the collection of cat allergen Fel d 1 from the environment: Investigation of capture material.

The device "Ionic Breeze Air Freshener for Bathrooms and Small Spaces", Model IU627JPN was used as a testbed. The removable electrode dimensions are 8 cm×1.3 cm. Silk is obtained from Dharma Trading Company, San Rafael, Calif., Silk Habotai #HS1055. Rectangles are cut from the silk so as to create pockets that exactly envelope the electrodes. Seams are sewn at 7 cm apart so that the silk is stretched taut over the electrodes. The device was run for 16 hrs in the presence of cats. A control was run in parallel with no cover on the electrodes. ELISA kits for the cat allergen Fel d 1, Product Code: EL-FD1, are obtained from Indoor Biotechnologies, Charlottesville, Va. The silk capture material is carefully removed from the electrodes with a forceps immediately on turning off the power, with minimum agitation, and placed in a 16 ml Falcon tube. The silk is immersed in 1.0 ml of PBS-0.05% tween as described in the package insert of the ELISA. The electrodes of the control device are similarly carefully removed on turning off the power, without tipping or shaking, and wiped down with a 10.5 cm×11 cm piece of Kleenex tissue, folded in half and wrapped around the tip of a forceps, previously wetted with the same buffer. The tissue is also place in a Falcon tube and thereafter both sample and control are treated identically. The samples are assayed undiluted and through 10 2-fold serial dilutions, as are the standards provided with the kit. At the end of the ELISA assays, 30 minutes is allowed for color development and the developed color is quantitated in a Synergy H4 Hybrid Multi-Mode Microplate Reader at 405 nm. Results for two different sites, with different intensity of exposure to the cat allergens, are shown in FIG. 9. The recovery with silk as capture material is at least as good as the controls which are wiped down manually. The ability to use a capture material is clearly far more convenient than manual wiping. Further, neither air flow patterns nor velocity are significantly affected by the use of silk as a nonconductive capture material. Other materials that captured allergen less efficiently are rayon, cotton, and cellulose paper (Pall S70006). Silk gauze with very open weave, Dharma #SG36/45, behaves as well as the conventional silk. It is therefore likely that there is an induced charge in the non-conductive silk that serves to selectively attract charged particles from the air. PBS-Tween also performs better as a medium for solubilizing the allergen than water or PBS-Tureen containing 1% bovine serum albumin.

From the calibration curve performed in parallel with the ELISA of FIG. 9, the amount of the cat allergen Fel d 1 collected is 4 ng in 1 mL. The molecular weight of the allergen is 18 KDa. The concentration thus measured corresponds to $2.2\times10^{-10}$ M. Limits of detection in the range of $10^{-12}$ M have been achieved with lateral flow immunoassays (ref 1 above), while $10^{-8}$ M has been described for the Octet system (ref 6 above). The concentrations captured can clearly be increased considerably by decreasing the capture electrode size concomitantly with the capture material area. Further amplification can be obtained by the use of a sandwich format by means of a second, labeled antibody, which may be present in a dried form in the device. From the nature of the detection system, only binding events at the optical interface are detected, so no washing steps are required. The label may take the form of metal sols or polymers, and thus considerably increase the effective optical path created by the bound species.

Example 2 comprises Spectral shift determination with the use of imaging software.

A photograph of a neutral white surface is taken with a Canon Digital Rebel Model XSi with a 20 mm fixed focus lens at 1/60 sec and f/4 with flash. The image is saved as a "raw" file and opened with Adobe Bridge version CS5. The color temperature adjustment was set to adjust the apparent color temperature of the light source successively to 4000, 5000, 6000 and 8000° K, and for each the file is opened in Adobe Photoshop CS5. The histograms are obtained from the pull-down menu for "Window". Separate histograms for red, green and blue channels are obtained for each color temperature. Each histogram is a distribution of number of pixels at each intensity level from 1 to 255. The results are summarized in FIG. 9. As can be seen, the distribution skews to higher intensities for increasing color temperature for the red channel and lower intensities for the blue channel, while the green channel changes little. Means and standard deviations corresponding to the data of FIG. 9 are shown here:

| Color temperature | Red | | Green | | Blue | |
|---|---|---|---|---|---|---|
| | Mean | SD | Mean | SD | Mean | SD |
| 4000 | 89.17 | 31.76 | 107.07 | 35.22 | 141.96 | 42.44 |
| 5000 | 102.32 | 34.86 | 109.48 | 36.55 | 123.38 | 39.71 |
| 6000 | 112.21 | 36.98 | 110.81 | 36.99 | 110.69 | 37.06 |
| 8000 | 122.58 | 38.98 | 111.53 | 37.08 | 100.42 | 34.52 |

Thus, any spectral change in the captured image can be visualized and quantitated by algorithms already available in off-the-shelf software.

Thus, there is disclosed herein a device for determination of a sample from a dielectric fluid medium for a bio-specific assay device, comprising: a sampling device and a biosensor, wherein the sampling device concentrates a sample from dielectric medium by electrically focusing the sample on to a capture element and wherein said biosensor is fluidically linked to said capture element thus providing sampling and determination in a unitary device.

The sampling device may comprise an ionic propulsion device and focuses the sample on to a delimited area. The delimited area results in sample concentration and interrogation of a small volume thus resulting in improved sensitivity.

The biosensor may comprise an optical sensor device. The optical sensor device may be a white light interference spectroscopy device. The optical sensor device may be a fluorescent microparticle-based sensing system.

The biosensor may comprise an electrical sensing device, such as a field-effect transformer device or a magnetoresistive device.

The optical sensor device may measures shifts in wavelength light, optical interference, or color of fluorescent microparticles. The wavelength shift may be determined by means of a spectrophotometer, by a digital imaging device, or from color values of pixels.

There is also disclosed an optical biosensor device wherein molecular binding reactions are determined by analysis of spectral changes in digital images. The spectral changes may result from optical interference effects or from fluorescent microparticle binding reactions. The spectral changes may be determined from analysis of color value distributions of pixels.

It will be appreciated by those skilled in the art that there are many possible modifications to be made to the specific forms of the features and components of the disclosed embodiments while keeping within the spirit of the concepts disclosed herein. Accordingly, no limitations to the specific forms of the embodiments disclosed herein should be read into the claims unless expressly recited in the claims. Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A device for determination of a sample from a dielectric fluid medium for a bio-specific assay device, comprising: a sampling device and a biosensor, wherein the sampling device comprises an ionic propulsion device that concentrates a sample from dielectric fluid medium by electrically focusing the sample on to a delimited area of a capture element and wherein said biosensor is fluidically linked to said capture element thus providing sampling and determination in a unitary device.

2. A device according to claim 1 wherein the delimited area results in sample concentration and interrogation of a small volume thus resulting in improved sensitivity.

3. A device according to claim 1 wherein said biosensor comprises an optical sensor device.

4. A device according to claim 3 wherein said optical sensor device is a white light interference spectroscopy device.

5. A device according to claim 3 wherein said optical sensor device is a fluorescent microparticle-based sensing system.

6. A device according to claim 3 wherein the optical sensor device measures shifts in wavelength light.

7. A device according to claim 6 wherein the optical sensor device measures optical interference.

8. A device according to claim 6 wherein the optical sensor device measures color of fluorescent microparticles.

9. A device according to claim 8 wherein the wavelength shift is determined from color values of pixels.

10. A device according to claim 6 wherein the wavelength shift is determined by means of a spectrophotometer.

11. A device according to claim 6 wherein the wavelength shift is measured by a digital imaging device.

12. A device according to claim 1 wherein said biosensor comprises an electrical sensing device.

13. A device according to claim 12 wherein said electrical sensing device comprises a field-effect transistor device.

14. A device according to claim 12 where said electrical sensing device comprises a magneto-resistive device.

* * * * *